United States Patent [19]

Johnson

[11] Patent Number: 4,776,882
[45] Date of Patent: Oct. 11, 1988

[54] CONCENTRATED BASAL SPRAY

[75] Inventor: Roy R. Johnson, Ambler, Pa.

[73] Assignee: Rhone Poulenc Nederlands B.V., Amstelveen, Netherlands

[21] Appl. No.: 555,466

[22] Filed: Nov. 30, 1983

Related U.S. Application Data

[63] Continuation-in-part of Ser. No. 453,167, Dec. 27, 1982, abandoned.

[51] Int. Cl.$^4$ ............................................. A01N 25/00
[52] U.S. Cl. ......................................... 71/109; 71/94; 71/107; 71/108; 71/116; 71/117; 71/86; 71/DIG. 1
[58] Field of Search ..................... 71/86, DIG. 1, 110, 71/109, 107

[56] References Cited

U.S. PATENT DOCUMENTS 3,188,194  6/1965  d'Ogny ................................. 71/2.5

OTHER PUBLICATIONS

Chem. Abstr., vol. 67, 1967–99132n.
Chem. Abstr., vol 72–11624u.
Chem. Abstr., vol. 74, 1971–75608r.
Chem. Abstr., vol. 95, 1981–95:182281j.
Chem. Abstr., vol. 89, 1978–89:141823v.
Chem. Abstr., vol. 84, 1976–84:175103x.
Chem. Abstr., vol. 67, 1967–107586f.
Chem. Abstr., vol. 77, 1972–136163c.
Chem. Abstr., vol. 81, 1974–34550s.
Chem. Abstr., vol. 83, 1976–158998e.
Chem. Abstr., vol. 84, 1976–84:145913u.
Chem. Abstr., vol. 92, 1980–92:35994d.

Primary Examiner—Catherine L. Mills
Attorney, Agent, or Firm—Morgan & Finnegan

[57] ABSTRACT

This invention relates to the discovery that esters of phosphoric and phthalic acids are effective wood penetrant-carriers for biocidally active ingredients, especially oil soluble or oil miscible ingredients, in basal sprays.

31 Claims, No Drawings

CONCENTRATED BASAL SPRAY

The application is a continuation-in-part of Ser. No. 453,167, filed Dec. 27, 1982, now abandoned.

FIELD OF THE INVENTION

This invention relates to the use of phosphoric and/or phthalic acid esters as wood penetrants for biocidally active ingredients in basal spray compositions.

BACKGROUND OF THE INVENTION

The ability to control undesirable woody plants or undesirable fungus or pests in woody plants by individual stem applications of herbicides; plant growth regulators; fungicides; and insecticides rather than by broadcast foliar sprays is highly desirable from both economic and environmental considerations. Today, for example, controlling undesirable woody plants by individual stem applications of herbicides is an important tool for the effective management of woody vegetation on highway, public utility, railroad rights-of-way, and similar areas.

The application of high volume, oil miscible herbicide sprays diluted with fuel oil, kerosene, or other petroleum solvents has been the primary method of individual stem brush control since phenoxy herbicides were developed in the 1940's. However, recent increases in the cost of petroleum solvents have made this technique, called basal spraying, uneconomical.

Soil active herbicides, water/oil mixtures, and cut stem injection techniques such as frilling have been utilized in an attempt to find a replacement for the original high-volume oil, basal spray technique. All of these replacement techniques will afford some control of many woody plants, but they are subject to disadvantage such as high cost; injury to off-target vegetation from root uptake; limited use at below freezing temperatures; and the necessary use of sharp, dangerous tools to cut the woody plant stems.

It would be highly desirable to have a technique for realizing control of woody plants and undesirable organisms that infest said plants that obviated the aforementioned disadvantages, e.g., a low cost, low volume, injury specific application technique that could be utilized in any season without the use of dangerously sharp instruments.

SUMMARY OF THE INVENTION

This invention relates to the discovery that esters of phosphoric and phthalic acids are effective wood penetrant-carriers for fungicides, insecticides, herbicides, and plant growth regulators. The aforementioned penetrant-carriers are especially effective when the active ingredients are oil-soluble and/or oil miscible. Basal spray compositions using these penetrants can be effectively used (a) with 1/10 of the total conventional volume—thus eliminating the necessity of transporting large volumes of expensive fuel oil to the use site; (b) in any season—the absence of water eliminates freezing problems; and (c) with herbicides of limited soil activity thus eliminating or significantly reducing potential injury to off-target vegetation.

DETAILED DESCRIPTION OF THE INVENTION

This invention relates to compositions comprising a penetrant-carrier in combination with a herbicide, plant growth regulator, fungicide, or insecticide, all the aforementioned hereinafter generically referred to as biocides, and the use of this composition in a basal spray to control woody plants, regulate the growth of said plants or control organisms which infest said plants.

The term "basal spray" means that the composition is directly applied usually via conventional low volume spray apparatus, to the stem or bark of a woody plant, usually at the basal portion of the plant. Generally, the composition is sprayed onto from about a 12 to 36 inch portion of the lower end of the stem, i.e., that end of the stem closest to the ground or trunk.

The penetrants of this invention are (a) compounds of phosphorous having the formula:

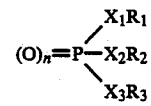

wherein $x_1$, $x_2$ and $x_3$ are individually O or S;

n is 0 or 1;

$R_1$ is selected from the group consisting of hydrogen, $C_1$ to $C_{10}$ alkyl, aryl, aryl-($C_1$-$C_{10}$)alkyl, cycloaliphatic, and heterocyclic; and $R_2$ and $R_3$ are individually selected from the group consisting of $C_1$-$C_{10}$ alkyl, aryl, aryl-($C_1$-$C_{10}$)alkyl, cycloaliphatic, and heterocyclic.

In other words, at least two of the groups attached to the oxygens/sulfurs connected by a single bond to the phosphorous group are organic groups, while the other is either an organic group or hydrogen.

(b) esters of phthalic acid having the formula

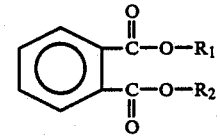

wherein $R_1$ and $R_2$ are individually selected from the group consisting of hydrogen, $C_1$-$C_{10}$ alkyl, aryl, and aryl-($C_1$-$C_{10}$)alkyl with the proviso that $R_1$ and $R_2$ cannot both be hydrogen, (c) and combinations of the above-described phosphoric and phthalic acid esters.

The preferred penetrant-carriers are the following:
symmetrical triaryl phosphate esters such
triphenyl phosphate;
tricresyl phosphate (all isomers); and
tri(O-cresyl)phosphate;
unsymmetrical triaryl phosphate esters such
cresyl diphenyl phosphate ester;
alkyl diaryl phosphate esters such as
2-ethylhexyl diphenyl phosphate;
dialkyl phosphate esters such as
dibutyl phosphate;
trialkyl phosphate esters such as
tributyl phosphate;
tridecyl phosphate;
triethyl phosphate; and
tri(2-ethylhexyl)phosphate;
trialkyl phosphorotrithioate esters such as
S,S,S, tributylphosphorotrithioate
trialkyl phosphorotrithioite esters such as tributyl phosphorotrithioite;
mono- and di-alkyl phthalate esters such as
dibutyl phthalate; and
dioctyl phthalate.

The most preferred penetrant-carrier of this invention is tributyl phosphate.

Although the effectiveness in basal sprays of most herbicides, fungicides, insecticides and plant growth regulators can be enhanced via the utilization of the penetrant-carriers of this invention, the preferred active ingredients are oil soluble or oil miscible.

The preferred active ingredients of this invention are, for example, herbicides which are phenoxy acids and esters such as:
2,4-dichlorophenoxypropionic acid, butoxy-ethanol ester,
2,4-dichlorophenoxyacetic acid, butoxy-ethanol ester,
2,4,5-trichlorophenoxyacetic acid, butoxy-ethanol ester,
2-(2,4,5-trichlorophenoxy)propionic acid,
4-(2,4-dichlorophenoxy)butyric acid,
4-chloro-1-methylphenoxyacetic acid,
4-(2-methyl-4-chlorophenoxy)butyric acid, and
2-(4-chloro-2-methylphenoxy)propionic acid.

Other preferred herbicides include
4-amino-3,5,6-trichloropicolinic acid,
2-methoxy-3,6-dichlorobenzoic acid, and
3,5,6-trichloro-2-pyridinyloxyacetic acid.

Combinations of the above with themselves or with other active ingredients can also be desirable since two or more of the effective, i.e. active, ingredients can be used in combination to increase the number of species of woody plants or plant pests which can be controlled.

This invention utilizes an amount of active biocide equivalent to that used in a conventional basal or stump spray for control of woody plants or plant pests but uses a significantly lower volume of penetrant-carrier or combination of carriers in lieu of the conventional larger volume of fuel oil or kerosene.

Whereas a conventional basal herbicidal spray would apply from 30 to 100 gallons per acre of a herbicide/oil mixture containing about 1 to 20, preferably about 5 to about 16 pounds of a herbicide, for example a phenoxy herbicide, with the instant invention only from about 1 to about 15, preferably from about 3 to 10 total gallons containing the same amount of active herbicide would be applied per acre. Usually the preferred amount of spray volume needed is about 1/10th the amount of active oil-carrier spray volume conventionally used.

In that the individual stems and/or trunks of plants are being treated with the biocide, the amount of active per acre is dependent on the amount of woody stem and/or trunk per acre. Therefore application rates are normally expressed as the amount applied per diameter-inch; either volume at a given concentration per diameter-inch or weight active per diameter inch.

Conventional basal sprays are usually applied at from about 120 ml to about 150 ml per diameter-inch with concentrations of from about 1.7 to about 2.3 weight percent of active ingredient based on the total weight. The basal sprays of this invention are usually applied at from about 10 to about 15 ml per diameter-inch at from about 12.5 to about 50 weight percent active based on the total weight of the composition, preferrably from about 22.8 to abut 35.6% by weight. In the case of esterified products, the weight percent is based on the ester.

A solvent diluent is preferably mixed with the active/penetrant combinations to solubilize the active and obtain desired active concentration for good spray distribution, i.e., good dispersion with conventional equipment.

Although many organic diluents would suffice—the choice being usually governed by economics—the preferred solubilizing diluents consist of about 90 percent naphthenic oil with the balance being kerosene.

The weight ratio of biocidally active ingredient to the penetrant should range from a minimum of about 1:30 to a maximum of about 20:1, preferably from about 1:10 to about 2:1 and most preferably from about 1:1.5 to about 1.5:1.

The solvent diluent is present in the basal concentrate at a weight ratio of solvent diluent to active biocidal ingredient at from about 0 to about 25, preferably from about 0.2 to about 10 and most preferably from about 0.5 to about 4 times the active ingredient.

The following examples are set forth for purposes of illustration so that those skilled in the art may better understand the invention, and it should be understood that they are not to be construed as limiting this invention in any manner.

EXAMPLE I

The compositions of the basal concentrate sprays used in this and the following examples are as follows:

| Ingredient | Percent By Weight |
|---|---|
| Composition A: | |
| 2,4-dichlorophenoxyacetic acid, butoxyethanol ester | 12.41 |
| 2-4-dichlorophenoxypropionic acid, butyoxyethanol ester | 12.99 |
| tributyl phosphate | 24.62 |
| naphthenic oil/kerosene solvent diluent | 49.98 |
| TOTAL | 100.00 |
| Composition B: | |
| 2,4,5-trichlorophenoxyacetic acid, butoxy ethanol ester | 22.82 |
| tributylphosphate | 24.50 |
| naphthenic oil/kerosene solvent diluent | 52.68 |
| TOTAL | 100.00 |
| Composition C: | |
| 2,4-dichlorophenoxyacetic acid, butoxyethanol ester | 9.25 |
| 2,4-dichlorophenoxypropionic acid butoxyethanol ester | 9.25 |
| 3,5,6-trichloro-2-pyridinyloxyacetic acid | 17.16 |
| tributylphosphate | 18.52 |
| naphthenic oil/kerosene solvent diluent | 45.82 |
| TOTAL | |
| Composition D: | |
| 2,4-dichlorophenoxyacetic acid, butoxyethanol ester | 9.31 |
| 2,4-dichlorophenoxypropionic acid butoxyethanol ester | 9.31 |
| 4-amino-3,5,6-trichloropicolinic acid | 9.25 |
| tributylphosphate | 18.60 |
| naphthenic oil/kerosene solvent diluent | 53.53 |
| TOTAL | |
| Control: Weedone 170 TM a woody plant herbicide sold by Union Carbide.* | |
| 2,4-dichlorophenoxypropionic acid butoxyethanol ester | 29.3 |
| 2,4-dichlorpheoxyacetic acid butoxyethanol ester | 29.9 |

| Ingredient | Percent By Weight |
|---|---|
| inert ingredients | 40.8 |
| TOTAL | 100.0 |

*Applied as a mixture of about 3 to 4 gallons in 100 gallons of oil as recommended, i.e., about 120 ml per diameter-inch at about 2.5 weight percent active based on the total composition.

In each of the following examples, the compositions of this invention were applied at about 12 ml per diameter-inch at about a 25 weight percent active based on the total composition.

The above-identified compositions were applied as a basal spray using conventional equipment to various trees in the spring (June) in Pennsylvania and Maryland with the following results:

| | PERCENT CONTROL* | | | | | | | |
|---|---|---|---|---|---|---|---|---|
| Composition | Red maple | A. elm | Persimmon | W. ash | Sycamore | R. oak | Pine | Spruce |
| A | 80 | 100 | 100 | 100 | 100 | 100 | 90 | 80 |
| B | 100 | 100 | 100 | 100 | 100 | 100 | 100 | 100 |
| C | 100 | 100 | 100 | 100 | 100 | 100 | 100 | 100 |
| D | 100 | 100 | 100 | 100 | 100 | 100 | 100 | 100 |
| Control | 70 | 100 | 100 | 80 | 100 | 90 | 70 | 60 |

*Evaluation was based on the amount of live growth remaining above the ground

EXAMPLE II

The following basal spray field trials were conducted in May in New York State with evaluations in August of the same year. All trials were with Composition C.

| SPECIES | PERCENT CONTROL |
|---|---|
| white ash | 98 |
| hickory | 90 |
| white pine | 98 |
| pin cherry | 100 |
| northern red oak | 80 |
| white oak | 100 |
| red maple | 100 |
| aspen | 100 |
| black locust | 97 |
| white birch | 98 |

EXAMPLE III

The following basal spray field trials were conducted in the spring and summer months in Virginia.

| | PERCENT CONTROL | |
|---|---|---|
| SPECIES | Comp. A | Comp. C |
| white oak | 98 | 100 |
| red oak | 98 | 87 |
| tulip-poplar | 100 | 100 |
| chestnut oak | 95 | 100 |
| Sassafras | 100 | 100 |
| hickory | 100 | 100 |
| sourwood | 42 | 100 |
| red maple | 100 | — |
| black cherry | 80 | 90 |
| black locust | 100 | 100 |
| black gum | 100 | — |
| sumac | 100 | — |
| persimmon | 90 | — |
| Ailanthus | 100 | 100 |

What is claimed is:

1. A method of controlling undesirable woody plants or plant pest organism which comprises basally spraying said woody plants or organism-containing plants with a mixture comprising:
   (a) from about 12.5 to about 50 weight percent based on the total composition weight of a herbicidally active ingredient; and
   (b) a penetrant-carrier comprising a compound selected from the group consisting of
      (1) compounds of the formula

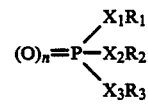

wherein
   $X_1$, $X_2$ and $X_3$ are individually O or S;
   n is 0 or 1;
   $R_1$ is selected from the group consisting of hydrogen, $C_1$ to $C_{10}$ alkyl, aryl, aryl-($C_1$-$C_{10}$)alkyl, cycloaliphatic and heterocyclic; and
   $R_2$ and $R_3$ are individually selected from the group consisting of $C_1$-$C_{10}$ alkyl, aryl, aryl-($C_1$-$C_{10}$)alkyl, cycloaliphatic, and heterocyclic;
   (2) compounds having the formula

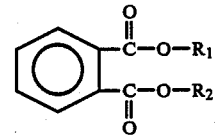

wherein
   $R_1$ and $R_2$ are individually selected from the group consisting of hydrogen, $C_1$-$C_{10}$ alkyl, aryl, and aryl-($C_1$-$C_{10}$)alkyl with the proviso that $R_1$ and $R_2$ cannot both be hydrogen; and
   (3) combinations thereof.

2. The method of claim 1 wherein said herbicidally active ingredient is a herbicide.

3. The method of claim 1 wherein said herbicidally active ingredient is a plant growth regulator.

4. The method of claim 1 wherein said penetrant-carrier comprises a compound selected from the group consisting of triphenyl phosphate; tricresyl phosphate; cresyl diphenyl phosphate; 2-ethylhexyl diphenyl phosphate; dibutyl phosphate; tributyl phosphate; tridecyl phosphate; triethyl phosphate; tri(2-ethylhexyl)phosphate; S,S,S,-tributylphosphorotrithioate; tributyl phosphorotrithioite; dibutyl phthalate; and dioctyl phthalate.

5. The method of claim 1 wherein said penetrant-carrier is tributyl phosphate.

6. The method of claim 1 wherein said herbicidally active ingredient is oil soluble or oil miscible.

7. The method of claim 1 wherein said mixture additionally contains an organic solvent diluent.

8. The method of claim 7 wherein said diluent comprises naphthenic oil.

9. The method of claim 1 wherein the weight ratio of said herbicidally active ingredient to said penetrant-carrier is from about 1:30 to about 20:1.

10. The method of claim 9 wherein said ratio is from about 1:10 to about 2:1.

11. The method of claim 9 wherein said ratio is from about 1:1.5 to about 1.5:1.

12. The method of claim 7 wherein the weight ratio of said diluent to said herbicidally active ingredient is from about 0 to about 25.

13. The method of claim 12 wherein said ratio is from about 0.2 to about 10.

14. The method of claim 12 wherein said ratio is from about 0.5 to about 4.

15. A method of controlling undesirable woody plants which comprises basally spraying said plants with a mixture comprising:
(a) from about 12.5 to about 50 percent by weight based on the total composition of a herbicide; and
(b) a penetrant-carrier comprising a compound selected from the group consisting of
(1) compounds of the formula

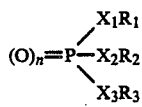

wherein
$X_1$, $X_2$ and $X_3$ are individually O or S;
n is 0 or 1;
$R_1$ is selected from the group consisting of hydrogen, $C_1$ to $C_{10}$ alkyl, aryl, aryl-$(C_1-C_{10})$alkyl, cycloaliphatic and heterocyclic; and
$R_2$ and $R_3$ are individually selected from the group consisting of $C_1-C_{10}$ alkyl, aryl, aryl-$(C_1-C_{10})$alkyl, cycloaliphatic, and heterocyclic;
(2) compounds having the formula

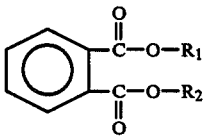

wherein
$R_1$ and $R_2$ are individually selected from the group consisting of hydrogen, $C_1-C_{10}$ alkyl, aryl, and aryl-$(C_1-C_{10})$alkyl with the proviso that $R_1$ and $R_2$ cannot both be hydrogen; and
(3) combinations thereof.

16. The method of claim 15 wherein said herbicide is oil soluble or oil miscible.

17. The method of claim 15 wherein said herbicide comprises a compound selected from the group consisting of herbicidally-active phenoxy acids; esters; and combinations thereof.

18. The method of claim 15 wherein said herbicide comprises a compound selected from the group consisting of
2,4-dichlorophenoxypropionic acid, butoxy-ethanol ester,
2,4-dichlorophenoxyacetic acid, butoxy-ethanol ester,
2,4,5-trichlorophenoxyacetic acid, butoxy-ethanol ester,
2-(2,4,5-trichlorophenoxy)propionic acid,
4-(2,4-dichlorophenoxy)butyric acid,
4-chloro-2-methylphenoxyacetic acid,
4-(2-methyl-4-chlorophenoxy)butyric acid, and
2-(4-chloro-2-methylphenoxy)propionic acid,
4-amino-3,5,6-trichloropicolinic acid,
2-methoxy-3,6-dichlorobenzoic acid,
3,5,6-trichloro-2-pyridinyloxyacetic acid,
and combinations thereof.

19. The method of claim 15 wherein said herbicide comprises 2,4,5-trichlorophenoxyacetic acid, butoxy-ethanol ester.

20. The method of claim 15 wherein said penetrant-carrier comprises a compound selected from the group consisting of triphenyl phosphate; tricresyl phosphate; cresyl diphenyl phosphate; 2-ethylhexyl diphenyl phosphate; dibutyl phosphate; tributyl phosphate; tridecyl phosphate; triethyl phosphate; tri(2-ethylhexyl)phosphate; S,S,S,-tributylphosphorotrithioate; tributyl phosphorotrithioite; dibutyl phthalate; and dioctyl phthalate.

21. The method of claim 15 wherein said penetrant-carrier is tributyl phosphate.

22. The method of claim 15 wherein said mixture additionally contains an organic solvent diluent.

23. The method of claim 22 wherein said diluent comprises naphthenic oil.

24. The method of claim 15 wherein the weight ratio of said herbicide to said penetrant-carrier is from about 1:30 to about 20:1.

25. The method of claim 24 wherein said ratio is from about 1:10 to about 2:1.

26. The method of claim 24 wherein said ratio is from about 1:1.5 to about 1.5:1.

27. The method of claim 22 wherein the weight ratio of said diluent to said herbicide is from about 0 to about 25.

28. The method of claim 27 wherein said ratio is from about 0.2 to about 10.

29. The method of claim 27 wherein said ratio is from about 0.5 to about 4.

30. A method in accordance with claim 1 wherein the herbicidally active ingredient is 2,4-dichlorophenoxypropionic acid, butoxyethanol ester and the penetrant-carrier is tributylphosphate.

31. A method of controlling undesirable plants which comprise basally spraying said plants with a mixture comprising:
(a) from about 12.5 to about 50 weight percent based on the total composition weight of 2,4,5-trichlorophenoxyacetic acid, butoxy ethanol ester; and
(b) tributylphosphate.

* * * * *